United States Patent
Kunz et al.

(10) Patent No.: US 10,441,396 B2
(45) Date of Patent: Oct. 15, 2019

(54) URETHRAL PLUG AND SYSTEM FOR ADDRESSING URINARY INCONTINENCE

(71) Applicant: Life360 Innovations Inc., Vancouver (CA)

(72) Inventors: Kenneth Kunz, Vancouver (CA); Robert Mitchell Orr, Vancouver (CA); Thom Bellaire, Vancouver (CA); Nigel Halsted, Vancouver (CA); Ernie Janzen, Vancouver (CA)

(73) Assignee: LIFE360 INNOVATIONS INC., Vancouver, BC (CA)

(*) Notice: Subject to any disclaimer, the term of this patent is extended or adjusted under 35 U.S.C. 154(b) by 198 days.

(21) Appl. No.: 15/683,124

(22) Filed: Aug. 22, 2017

(65) Prior Publication Data
US 2019/0060045 A1    Feb. 28, 2019

(51) Int. Cl.
*A61F 2/00*    (2006.01)

(52) U.S. Cl.
CPC .... *A61F 2/0009* (2013.01); *A61F 2210/0071* (2013.01); *A61F 2230/0067* (2013.01); *A61F 2230/0091* (2013.01); *A61F 2230/0093* (2013.01); *A61F 2250/0039* (2013.01); *A61F 2250/0059* (2013.01); *A61F 2250/0069* (2013.01); *A61F 2250/0078* (2013.01)

(58) Field of Classification Search
CPC ........ A61F 2/0022; A61F 2/0009; A61F 6/00; A61F 6/22; A61M 2210/1085
USPC ...................................................... 600/29–32
See application file for complete search history.

(56) References Cited

U.S. PATENT DOCUMENTS

| | | | |
|---|---|---|---|
| 2,649,854 A | 8/1953 | Salm | |
| 2,848,998 A | 8/1958 | Bryan | |
| 3,463,141 A | 8/1969 | Mozolf | |
| 3,648,683 A * | 3/1972 | Brodie | A61F 6/22 128/843 |
| 4,457,299 A | 7/1984 | Cornwell | |
| 4,934,999 A | 6/1990 | Bader | |
| 5,082,006 A * | 1/1992 | Jonasson | A61F 2/0022 128/885 |
| 5,090,424 A | 2/1992 | Simon et al. | |

(Continued)

FOREIGN PATENT DOCUMENTS

| | | |
|---|---|---|
| DE | 10304614 A1 | 8/2004 |
| EP | 0193406 A2 | 9/1986 |
| WO | 92/19192 A1 | 11/1992 |

OTHER PUBLICATIONS

Dribblestop Product information downloaded from http://www.incontinenceclamp.com/product.php?gclid=CLHvua-Wj6UCFRhzgwodlwx5Mg on Jul. 11, 2010; 1 page.

(Continued)

*Primary Examiner* — Samuel G Gilbert
(74) *Attorney, Agent, or Firm* — Schwabe Williamson & Wyatt, PC

(57) ABSTRACT

A urethral plug having a plug body, a lanyard and a stopper. The plug body having a leading end shaped to spread tissue at the urethral, a central portion; a trailing end tapering down from the central portion, and a sealing ring encircling the central portion. The plug body is shaped so that when positioned within the urethra the plug body is retained within the urethra, to restrict urine flow within the urethra past the plug body.

17 Claims, 13 Drawing Sheets

(56) References Cited

U.S. PATENT DOCUMENTS

| | | | |
|---|---|---|---|
| 5,131,906 A * | 7/1992 | Chen | A61F 2/0013 |
| | | | 128/DIG. 25 |
| 5,140,999 A | 8/1992 | Ardito | |
| 5,498,252 A | 3/1996 | Silber | |
| 5,509,427 A | 4/1996 | Simon | |
| 5,513,659 A | 5/1996 | Buuck | |
| 5,562,599 A * | 10/1996 | Beyschlag | A61F 2/0009 |
| | | | 600/29 |
| 5,630,429 A | 5/1997 | Dann | |
| 5,671,755 A | 9/1997 | Simon | |
| 5,701,914 A | 12/1997 | Loeffler | |
| 5,752,525 A | 5/1998 | Simon et al. | |
| 5,759,194 A | 6/1998 | Harnmerslag | |
| 5,884,629 A | 3/1999 | O'Brien | |
| 5,906,575 A * | 5/1999 | Conway | A61F 2/0022 |
| | | | 600/29 |
| 5,954,688 A | 9/1999 | Adams | |
| 5,971,967 A | 10/1999 | Willard | |
| 5,989,230 A | 11/1999 | Frassica | |
| 6,080,142 A | 6/2000 | Sachse | |
| 6,558,370 B2 | 5/2003 | Moser | |
| 6,695,763 B2 | 2/2004 | Zunker et al. | |
| 6,911,001 B2 | 6/2005 | Zunker | |
| 7,108,655 B2 | 9/2006 | Whalen et al. | |
| 7,255,673 B2 | 8/2007 | Ulmsten | |
| 7,655,021 B2 | 2/2010 | Brasington et al. | |
| 7,771,344 B2 | 8/2010 | Ziv | |
| 9,707,065 B2 | 7/2017 | Kunz | |
| 2004/0122285 A1 | 6/2004 | Zunker | |
| 2006/0079835 A1 | 4/2006 | Frassica | |
| 2006/0195006 A1 | 8/2006 | Daurell et al. | |
| 2007/0078389 A1 | 4/2007 | Whalen et al. | |
| 2008/0009931 A1 | 1/2008 | Bartning et al. | |
| 2009/0203959 A1 | 8/2009 | Ziv | |
| 2011/0028778 A1 | 2/2011 | Kunz | |

OTHER PUBLICATIONS

Datamonitor, "Pipeline and Commercial Insight: Urinary Incontinence," 185 pages, published Dec. 2007.

* cited by examiner

100

URETHRAL PLUG AND SYSTEM FOR ADDRESSING URINARY INCONTINENCE

TECHNICAL FIELD

The present disclosure relates to a device for controlling or mitigating urinary leakage associated with urinary incontinence and the methods associated with the use of same.

BACKGROUND

Urinary incontinence, or the loss of bladder control, is a common and potentially embarrassing problem. Urinary incontinence is not just a medical problem; it can affect emotional, psychological and social life. Many people who have urinary incontinence are afraid to conduct normal daily activities. The common ways to deal with urinary incontinence include collecting systems, absorbent products, fixed-occlusion devices, and indwelling catheters.

Absorbent products (including shields, undergarments, protective underwear, briefs, diapers, adult diapers, and underpants) are the best known product types to manage incontinence. They are generally easy to acquire in pharmacies or supermarkets. The disadvantages with absorbent products are that they can be bulky, leak, have odors, and can cause skin breakdown.

Collecting systems typically consist of a sheath worn over the penis funneling the urine into a urine bag worn on the leg. These products come in a variety of materials and sizes for individual fit. The disadvantages of these products are that it is necessary to get measured to ensure proper fit and you need a health care professional to write a prescription for them.

Fixed-occlusion devices (for men) are strapped around the penis, softly pressing the urethra and stopping the flow of urine. This management solution is only suitable for light or moderate incontinence.

Indwelling catheters (also known as Foley catheters) are very often used in hospital settings or if the user is not able to handle any of the above solutions. The indwelling catheter is typically connected to a urine bag that can be worn on the leg or hang on the side of the bed. Indwelling catheters need to be changed on a regular basis by a health care professional. The disadvantage, however, is that it is very common to get urinary tract infections when using indwelling catheters.

Intermittent catheters are single use catheters that are inserted into the bladder to empty it, and once the bladder is empty they are removed and discarded. Intermittent catheters are primarily used for retention (inability to empty the bladder) but for some people can be used to reduce/avoid incontinence.

BRIEF DESCRIPTION OF THE DRAWINGS

Embodiments will be readily understood by the following detailed description in conjunction with the accompanying drawings and the appended claims. Embodiments are illustrated by way of example and not by way of limitation in the figures of the accompanying drawings.

DETAILED DESCRIPTION OF DISCLOSED EMBODIMENTS

Figure 1A:
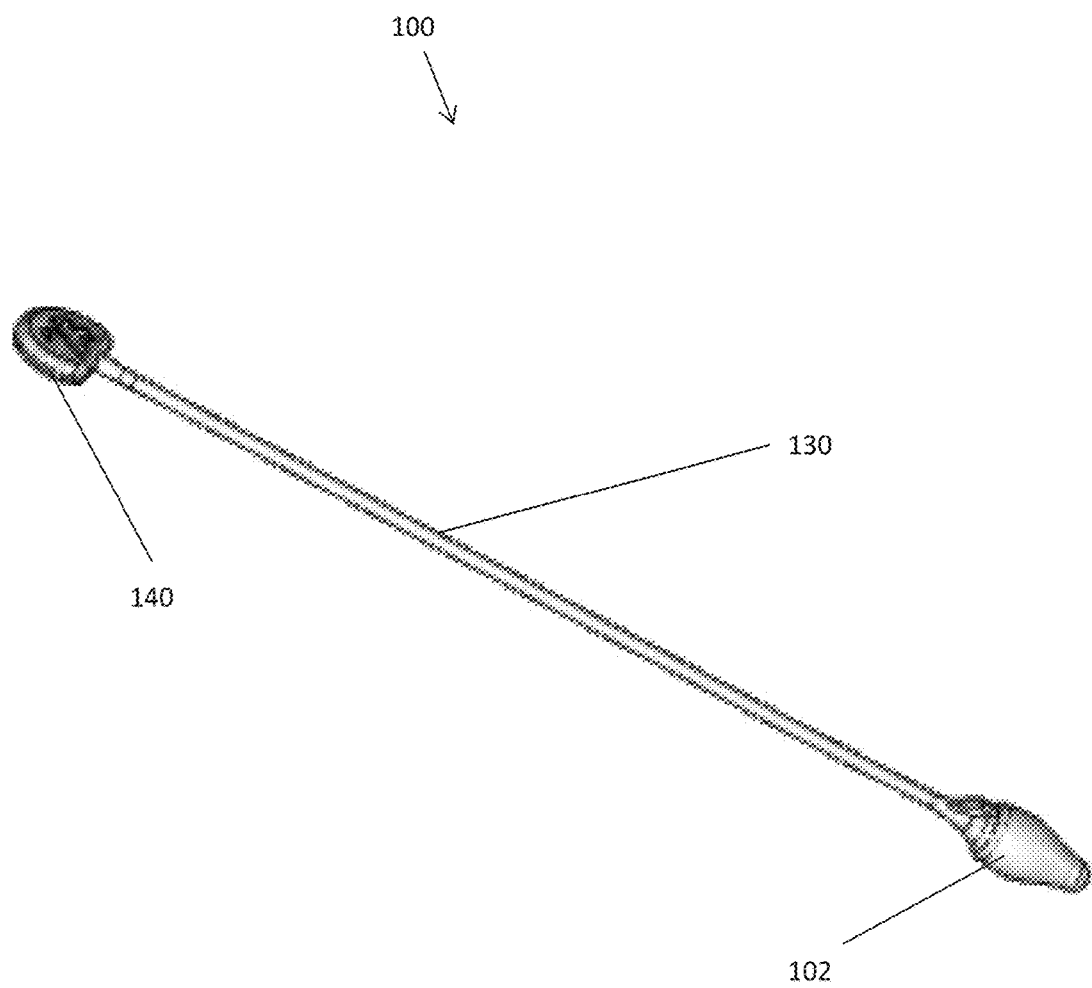
FIG. 1A is a perspective view of a urethral plug, in accordance with disclosed embodiments.

In the following detailed description, reference is made to the accompanying drawings, which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The description may use perspective-based descriptions such as up/down, back/front, and top/bottom. Such descriptions are merely used to facilitate the discussion and are not intended to restrict the application of disclosed embodiments.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments.

Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Globally, up to 35% of the population over the age of 60 years is estimated to be incontinent. It has been estimated that twenty-four percent of older adults in the U.S. have moderate or severe urinary incontinence that should be treated medically. Bladder control problems have been found to be associated with higher incidence of many other health problems such as obesity and diabetes. Difficulty with bladder control results in higher rates of depression and limited activity levels. Incontinence is expensive both to individuals in the form of bladder control products and to the health care system and nursing home industry. Injury related to incontinence is a leading cause of admission to assisted living and nursing care facilities. Both women and men can become incontinent from neurologic injury, congenital defects, strokes, multiple sclerosis, and physical problems associated with aging.

Men tend to experience incontinence less often than women, and the structure of the male urinary tract accounts for this difference. However, urinary incontinence is common in males having undergone prostate cancer treatments, for example surgical resection and/or radiation treatment. While urinary incontinence affects older men more often than younger men, the onset of incontinence can happen at any age. Estimates in the mid-2000s suggested that 17 percent of men over age 60, an estimated 600,000 men, experienced urinary incontinence, with this percentage increasing with age. Thus, there is a persistent need for a urethral plug that can be easily purchased and that is uncomplicated and user-friendly. Such a urethral plug would allow a user to have a normal quality of life and not be hindered by urinary leakage.

Embodiments of the present disclosure relate to a device for controlling or mitigating urinary leakage associated with urinary incontinence and the methods associated with the use of same. As disclosed herein, the device is comfortable to use and can prevent urinary leakage throughout the day and night. The disclosed device is configured so that optimally it only needs to be removed for the user to urinate. The device is simple in design and can be inserted by the user without any assistance from others. Insertion and removal of the device is easy and straightforward. When a user needs to relieve his bladder, the device is easily removed and can be washed with soap and water and dried prior to re-insertion. The whole process of removing the device, urinating and re-inserting a cleaned device, lubricating the meatus takes less than about four minutes.

The device can be repeatedly inserted and removed throughout the day and night with no discomfort, soreness or inflammation. The same device, in one embodiment, may be reusable by a single user up to 30 daily uses (i.e. a single use or multiple uses in the same 24 hour period are considered a single day's use). The device may last well beyond the recommended 30 days of use (i.e. up to 2 years), however for the user's health, we are recommending the device be replaced after 30 days of use. Alternatively, the device may be disposable and intended for a single use. By using the device, a user can lead a normal lifestyle and can participate in any type of recreational activity, including walking, running, biking and swimming, without the discomfort of being in wet, urine-smelling clothing. The device is not limiting on a user's mobility and is not uncomfortable to wear. The presence of the device in the urethral canal is imperceptible to a user and is not visible to others.

As disclosed herein, the urethral plug for addressing urinary incontinence includes a plug body, a lanyard or rip cord, and a stopper or pull tab/release handle. An example plug body starts with a round, approximately hemispherical, tip, which acts as a tissue spreader for ease of insertion into the urethral meatus. In embodiments, the urethral meatus may be lubricated prior to inserter to ease insertion. After the round tip, the plug body tapers gradually up to it maximum diameter at the maximum axis located approximately at the middle of the plug body. It is this portion of the plug body that reflects that maximum diameter of the device and corresponds with the French Catheter Scale. The entire plug head when set properly occludes the urethra as the urethra completely collapses around the plug head. In embodiments, the taper gradual transitions from a concave surface to a convex surface as it transitions from the round tip to the maximum axis. In embodiments, the plug body then tapers down to the back of the plug body to a transition point that connects with the lanyard. As the plug body tapers down, the tapered portion passes through a sealing ring or o-ring that has a maximum diameter slightly less than the maximum diameter (for example one French Catheter Scale value less than the plug size) at the largest extension of the middle of the plug body. The sealing ring can be considered part of the plug body. In embodiments, this sealing ring is part of a single unitary body with the remainder of the plug body, i.e. it is a single piece of material, such as a molded or formed device. In embodiments, the diameter of the plug body at its maximum diameter is between about 3 mm and about 16 mm, such as about 3.0 mm, 3.1 mm, 3.2 mm, 3.3 mm, 3.5, mm 3.6 mm, 3.7 mm, 3.8 mm, 3.9 mm, 4 mm, 4.1 mm, 4.2 mm, 4.3 mm, 4.5, mm 4.6 mm, 4.7 mm, 4.8 mm, 4.9 mm, 5 mm, 5.1 mm, 5.2 mm, 5.3 mm, 5.5, mm 5.6 mm, 5.7 mm, 5.8 mm, 5.9 mm, 6 mm, 6.1 mm, 6.2 mm, 6.3 mm, 6.5, mm 6.6 mm, 6.7 mm, 6.8 mm, 6.9 mm, 7 mm, 7.1 mm, 7.2 mm, 7.3 mm, 7.5, mm 7.6 mm, 7.7 mm, 7.8 mm, 7.9 mm, 8 mm, 8.1 mm, 8.2 mm, 8.3 mm, 8.5, mm 8.6 mm, 8.7 mm, 8.8 mm, 8.9 mm, 9 mm, 9.1 mm, 9.2 mm, 9.3 mm, 9.5, mm 9.6 mm, 9.7 mm, 9.8 mm, 9.9 mm, 10 mm, 10.1 mm, 10.2 mm, 10.3 mm, 10.5, mm 10.6 mm, 10.7 mm, 10.8 mm, 10.9 mm, 11 mm, 11.1 mm, 11.2 mm, 11.3 mm, 11.5 mm, mm 11.6 mm, 11.7 mm, 11.8 mm, 11.9 mm, 12 mm, 12.1 mm, 12.2 mm, 12.3 mm, 12.5, mm 12.6 mm, 12.7 mm, 12.8 mm, 12.9 mm, 13 mm, 13.1 mm, 13.2 mm, 13.3 mm, 13.5, mm 13.6 mm, 13.7 mm, 13.8 mm, 13.9 mm, 14 mm, 14.1 mm, 14.2 mm, 14.3 mm, 14.5, mm 14.6 mm, 14.7 mm, 14.8 mm, 14.9 mm, 15 mm, 15.1 mm, 15.2 mm, 15.3 mm, 15.5, mm 15.6 mm, 15.7 mm, 15.8 mm, 15.9 mm, and about 16 mm. In embodiments, the diameter of the round tip is between about 2 mm and about 5 mm, such as 2 mm, 2.5 mm, 3 mm, 3.5 mm, 4 mm, 4.5 mm, and 5 mm.

Typically, the plug body is sized appropriately for the individual wearer by a medical professional or by the user with a sizing kit, using the French Catheter Scale, for example sized using a urethral sound or other device such as a contino gauge. The urethral plug body is selected for use by a particular subject such that the diameter of the central axis of the plug body is slightly larger than the relaxed, internal diameter of the urethral canal of the wearer within the glans penis (i.e. penis head). The tissue around the glans penis is very dense and is not very distensible unlike the urethral canal within the penile urethra. Because the wall of the penile urethra is flexible and stretchable (i.e. distensible), a slightly oversized plug body is selected to provide the tight fit necessary to prevent urine leakage. When the plug body is positioned in the desired location in the urethral canal of a user, the plug body, in conjunction with the sealing ring, surface finish, and plug material properties (i.e. hydrophilic) provides a temporary seal in the urethral canal to prevent urinary leakage from the urethra. The additional tension of the wall of the urethra around the plug body further holds and secures the plug body in the proper position within the urethra.

Figure 10:
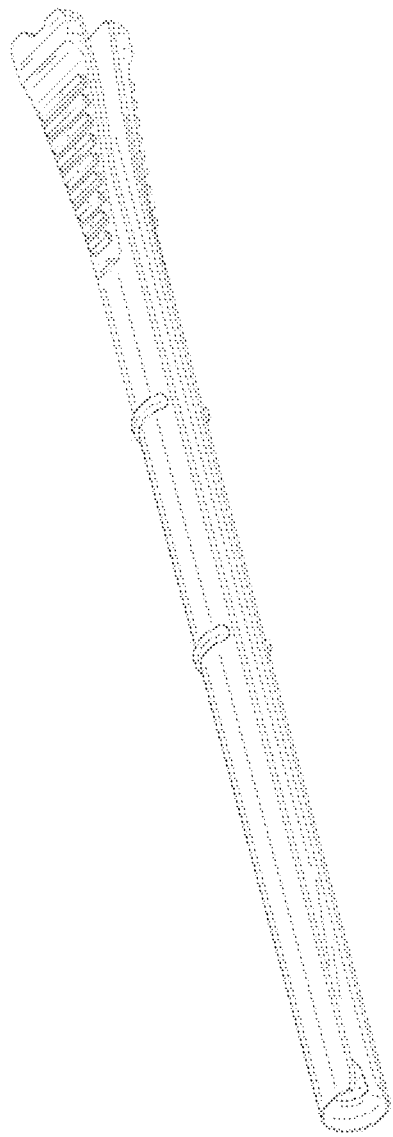
FIG. 10 depicts an inserter for use with the disclosed urethral plug.

In embodiments, the plug body includes a tab on the trailing end, this tab is positioned to fit within a slot in the urethral plug inserter as shown in FIG. 10. The tab includes a top surface that is relatively parallel to the long (tip-to-tail) axis of the plug body. The tab tapers upward to the top surface from the connection point of the lanyard.

In one embodiment, the plug body is non-absorbent and is made from a hard material, for example thermoplastic polymer, glass, hard rubber, or rigid plastic such that the device head has little to no bend or flex on insertion. Alternatively, the plug body is made from a flexible material and is pliable. In embodiments, the plug body is injection molded and constructed from suitable materials, such as a thermoplastic polymer. In certain embodiments, the plug body is made from a thermoplastic polymer. In certain embodiments, the plug body has a durometer hardness of between about 50 and about 90, such as about 50, about 55, about 60, about 65, about 70, about 75, about 80, about 85 or about 90. In embodiments, the plug body or the entire urethral plug may be non-hollow. In alternate embodiments, a portion of the plug body and the lanyard have an internal channel, for example for an internal inserter.

The outer surface of the plug body is typically made from a material that facilitates the anchoring of the device in the desired position in the urethral canal of a user. The plug body is preferably a material that enables the reduction of friction between the device and the wall of the urethra during insertion but also assists in maintaining the device in the proper position within the urethral canal. In certain embodiments, the plug body is a hydrophilic material. One of the unexpected properties of using a hydrophilic material is that it interacts well with the hydrophobic urethra (i.e. low friction on tissue with a hydrophobic counter-face). While most medical devices used in an urethral application are hydrophobic to prevent adhesion, in the context of a urethra plug, some adherence is desirable to get the added benefit of a tighter, more water tight temporary seal. In certain embodiments, the plug body has a surface finish designation from about B-1 to about C-3 as set forth in the SPI guidelines for surface finish, for example the plug body has a surface finish designation of B-1, B-2, B-3, C-1, C-2 or C-3. In a specific embodiment, the plug body has a surface finish designation of B-3.

As disclosed herein, in embodiments, the urethral plug includes a lanyard coupled to the trailing end of the plug body. The lanyard is a flexible material used for removal, a portion of which remains outside of the urethra while the plug body is "in situ" in the urethra (see FIG. 8). At the end of the lanyard there is a stopper or handle. The stopper can be any shape, for example, a ball, a tab or T-bar. The stopper is used to hold the device in place while assembled on the inserter, for example, shown in FIG. 9, for insertion. The stopper further prevents migration of the urethral plug into the urethra while in situ and facilitates removal for example by providing a graspable handle. In embodiments, the lanyard is sized so that a portion remains exterior to the penis when the plug body is appropriately situated in the urethra. In embodiments, the lanyard is a solid material and made as part of a unitary body with the plug body and/or the stopper. In certain embodiments, the stopper is a flat modified circular shape having a flattened portion that faces the plug body. The flattened circular portion includes a front face and a rear face to provide a place for the user to grab when removing the device as well as a place for directions and/or sizing information. The flattened portion of the circle is used to hold the device in place while assembled on the inserter for insertion. In embodiments, the lanyard is preferably a strong, durable string, cord, shaft, thread or ribbon capable of being sanitized. A person skilled in the art would understand that the lanyard may be constructed from any other suitable strong, durable material. In embodiments, when the urethral plug is properly positioned in the urethral canal of a user, the lanyard has a length that extends beyond the urethral canal, exterior to the urethral meatus. This length is preferably from between about 100 mm and about 200 mm, more preferably from between about 125 mm and about 175 mm, and even more preferably from between about 135 mm and about 160 mm.

In certain embodiments, the plug body is comprised primarily of medical grade silicone inside of which reside two cast medical grade epoxy anchors that are connected by a surgical ultra-high tensile strength braided lanyard. The cast epoxy anchors when connected together by the lanyard create a structural member that has been demonstrated to withstand tensional loading pressures of approximately 1000 lbs/int before failure.

In certain embodiments, the plug body includes at least two sealing rings, such as between 2 and 6 sealing rings, and a central recess between each of the rings. In embodiments, the sealing rings are separated by a distance from each other and each have a diameter larger than a diameter of the recess therebetween. In embodiments, the 4 to 6 sealing rings are of configured to look like a honey dipper. In certain embodiments, the sealing ring is configured as a helix with between about 2 and 6 helical turns. In certain embodiments, the central portion includes a reversible cone having sufficient flexibility to reverse its directional orientation as a result of a change in directional movement of the plug body with the urethra.

Figure 1B:
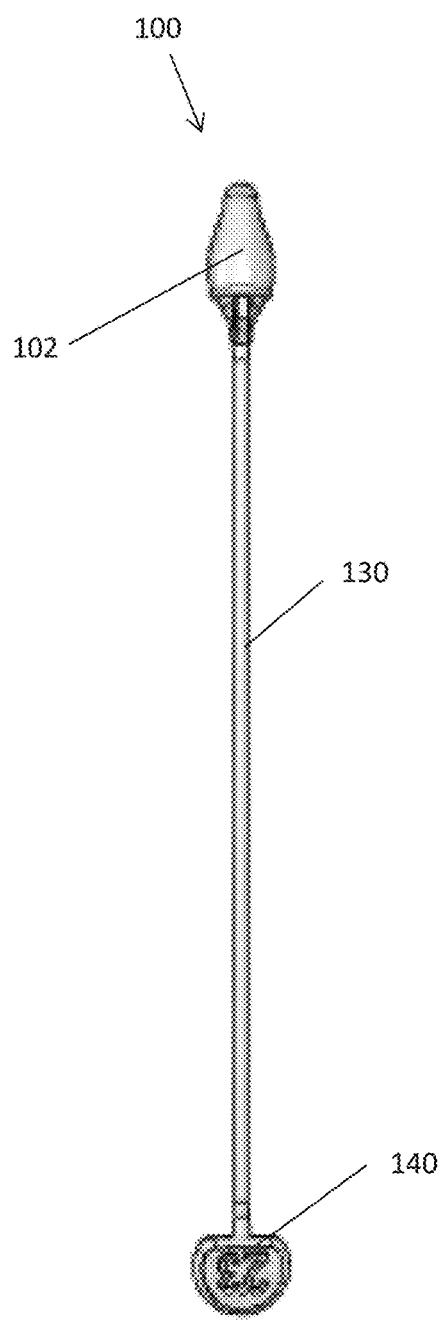
FIG. 1B is a top view of the urethral plug, in accordance with disclosed embodiments.
Figure 1C:
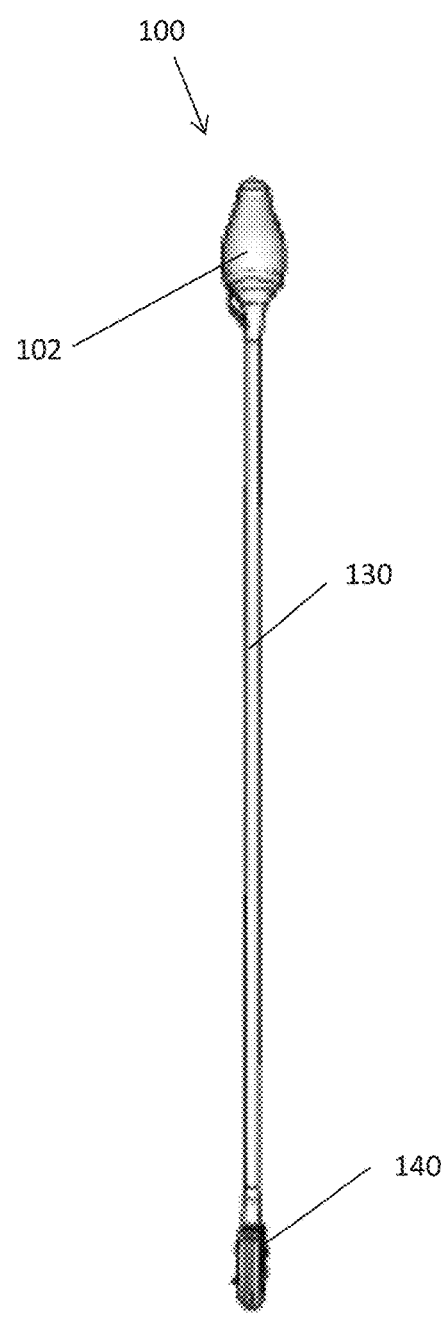
FIG. 1C is a side view of the urethral plug, in accordance with disclosed embodiments.

With reference to FIGS. 1A-1B an exemplary urethral plug 100 is provided. FIG. 1A shows a perspective view of a urethral plug 100, in accordance with disclosed embodiments. FIG. 1B shows a top view of the urethral plug of FIG. 1A. FIG. 1C shows a side view of the urethral plug of FIG. 1A. Urethral plug 100 includes three basic components, a plug body 102, a lanyard 130 and a stopper 140. The urethral plug 100 may be intended for a single use. Preferably, the urethral plug 100 may be reusable. In embodiments, such as shown in FIGS. 1A-1B, urethral plug 100 is non-hollow. As shown, plug body 102 may have a smooth outer surface.

Figure 2A:
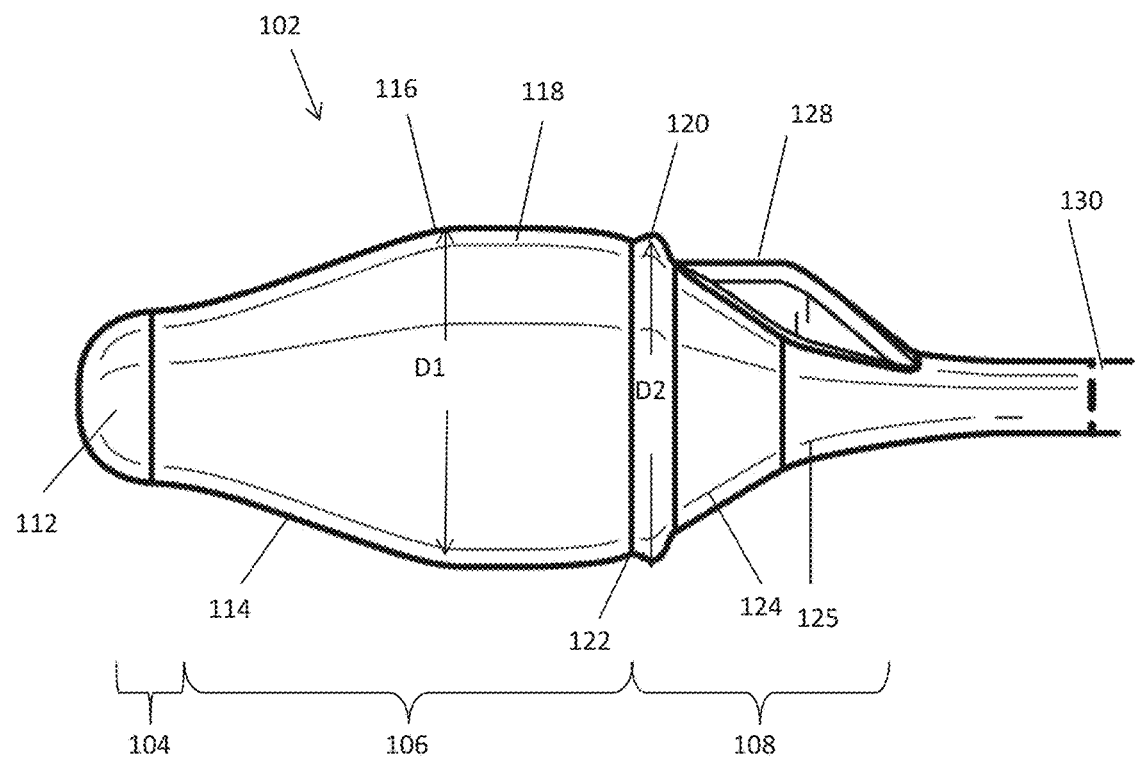
FIG. 2A is a side view of a plug body of the urethral plug, in accordance with disclosed embodiments.
Figure 2B:
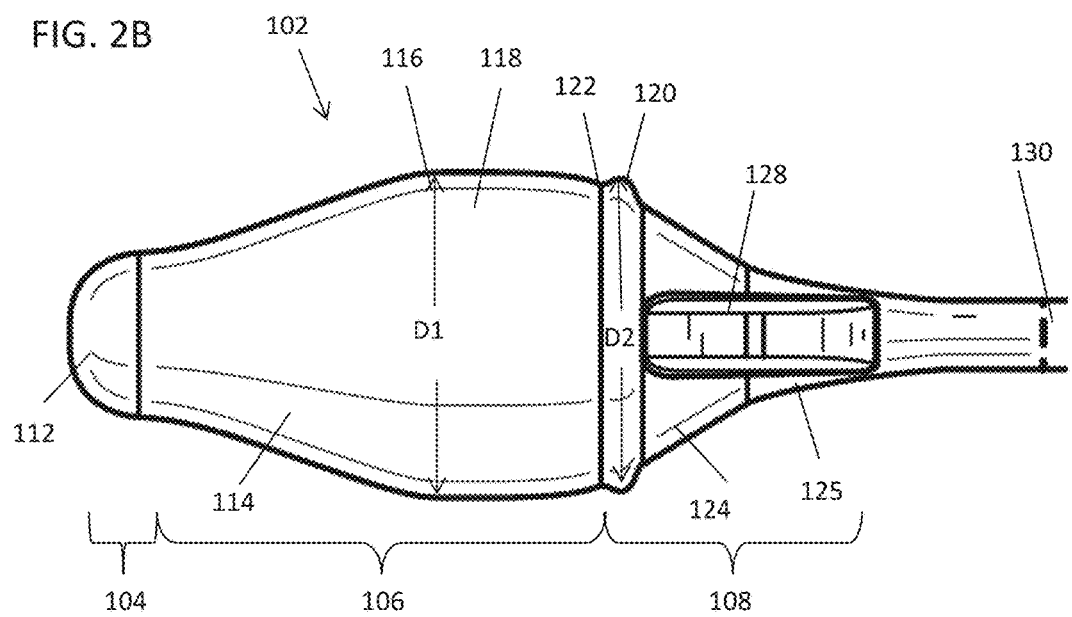
FIG. 2B is a top view of a plug body of the urethral plug, in accordance with disclosed embodiments.
Figure 2C:
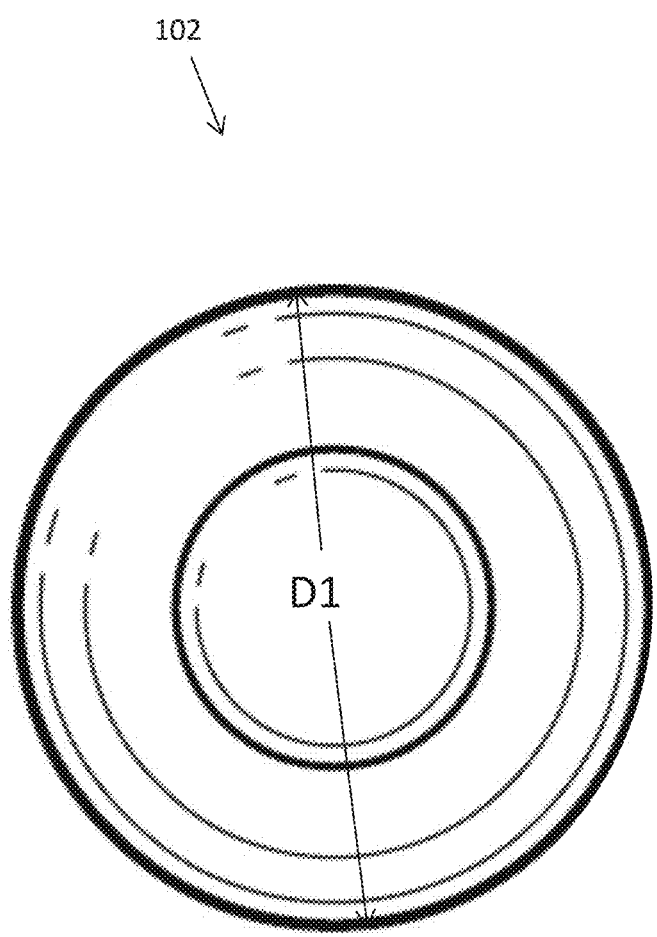
FIG. 2C is a front end view of the plug body of the urethral plug, in accordance with disclosed embodiments.
Figure 3A:
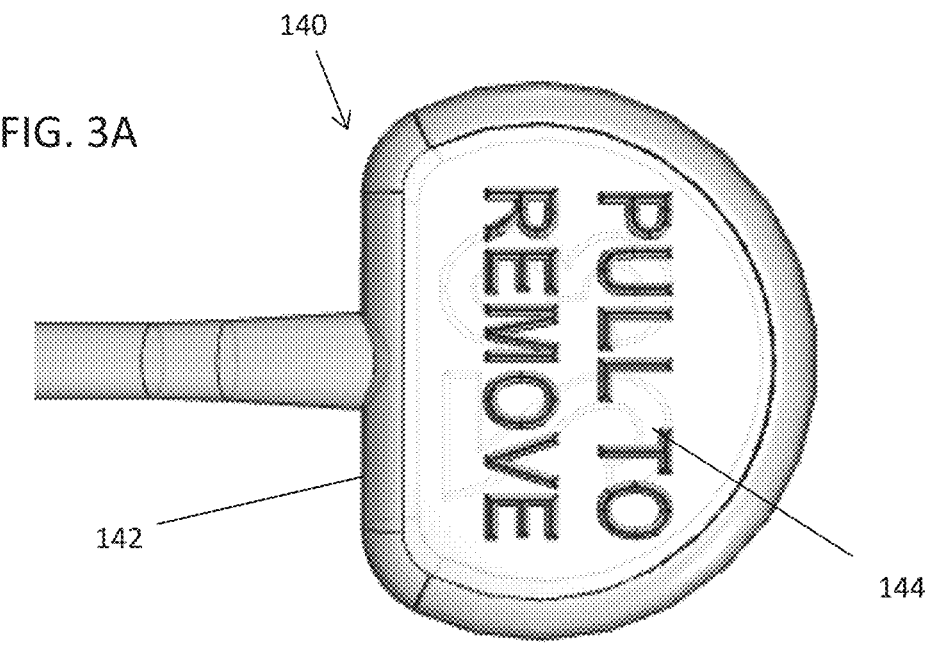
FIGS. 3A-3D are several views of the tail section of the urethral plug, in accordance with disclosed embodiments.
Figure 3B:
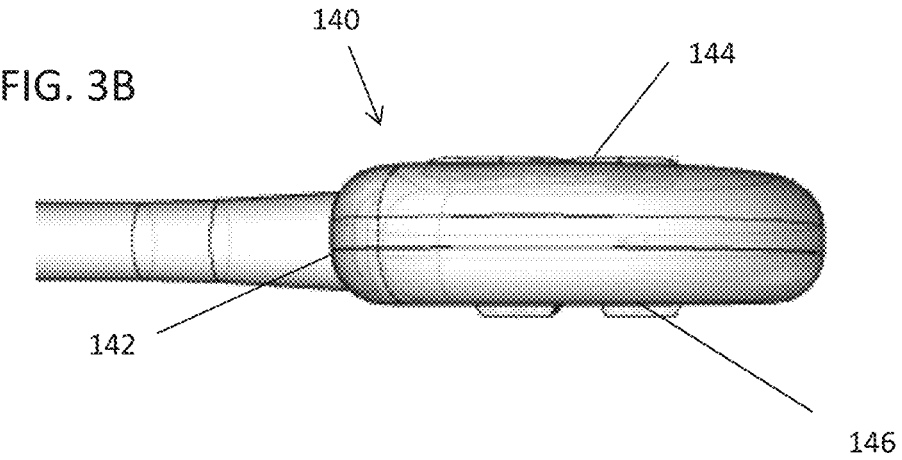
Figure 3C:
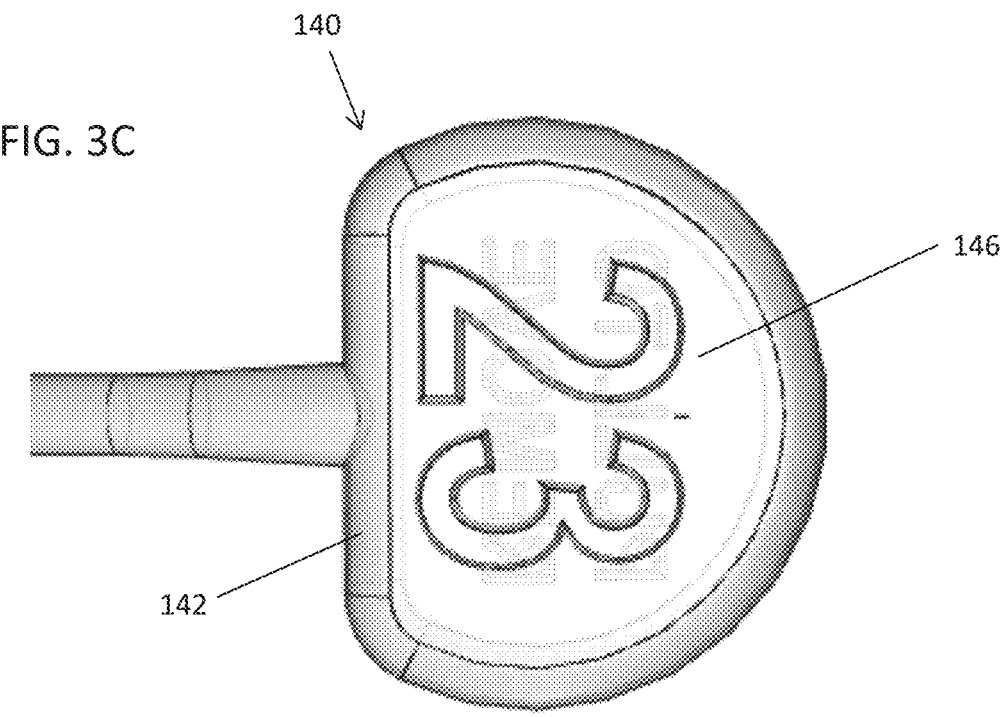
Figure 3D:
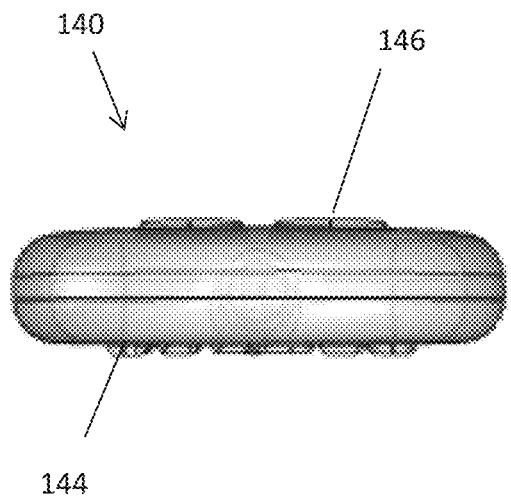

FIGS. 2A-2C show close up views of the plug body 102, of the urethral plug. FIG. 2A is a side view of the plug body 102 of the urethral plug. FIG. 2B is a top view of the plug body 102 of the urethral plug. FIG. 2C is a front end view of the plug body 102 of the urethral plug. The plug body 102 includes a leading end 104, a central portion 106, and a trailing end 108. The plug body 102 starts at the leading end 104 with tip 112, that is generally round, for example having a hemispherical appearance. The general round shape of the tip 112 acts as a tissue spreader for ease of insertion into the distal end of the urethra (distal meaning the urethral opening). The plug body 102 gradually tapers at 114 to the maximal diameter D1 at a central extension 116 that is located approximately at the middle of the plug body 102. The central portion 106 can have a generally bulbous and curved shape. The central extension 116 has a generally larger diameter than leading end 102 and trailing end 108. In combination with other elements, the diameter D1 at the central extension 116 is sized to occlude the urethra. In the embodiment shown, the plug body 102 slightly tapers down at 118 before meeting a sealing ring 120 at junction 122. After passing through the sealing ring 120, the plug body 102 tapers down at 124 and 125 to the back of the plug to a transition point that connects with the lanyard 130. Also shown is the positioning tab 128 which is shaped to fit into a slot in the inserter (not shown in this view). Tab 128 is a protrusion from the trailing end 108 of plug body 102 that constrains rotation of the urethral plug within the inserter and aligns the urethral plug such that the stopper 140 is in a desired position, such as to align with securing features on the end of the inserter. By way of example, without the tab 128 the plug body 102 would otherwise rotate within the inserter causing the lanyard 130 to twist as plug body 102 itself would not rotate while it is being inserted into the urethra due to friction with the urethra. Thus, absent the tab 128 the plug body 102 cannot easily be twisted or rotated to aid in insertion.

As shown in these views, the central portion 106 of the plug body 102 includes the sealing ring 120 having a diameter D2. The sealing ring 120 is located at the transition between the central portion 106 and the trailing end 108 and after the central portion 106 begins to taper down toward the lanyard 130. This unique feature aids in seating of the plug body 102 into the urethra of the wearer. In conjunction with the remainder of the plug body 102, the sealing ring 120 works to create a tighter seal in the urethra and thereby prevent urine from moving around the plug body 102. In addition, the trailing end 108 of the plug body 102 and the sealing ring 120 provides additional feedback to the user when setting the device according to the setting methodology.

As discussed, the plug body 102 has a diameter D1 at the central extension 116. In embodiments, the diameter D1 at the central extension 116 is greater than the diameter D2 of the sealing ring 120. Typically, the plug body 102 is sized appropriately for the individual wearer, for example using the French Catheter Scale. Typically, the urethral plug is selected such that the diameter D1 of the central extension 116 of plug body 102 is slightly larger than the relaxed urethra meatus The penile urethra is flexible and can stretch to accommodate the diameter D1 on insertion of the device 100 through the glans penis. When the plug body 102 is positioned in the desired location in the urethral canal of a user, the plug body 102 provides a seal in the urethral canal to prevent urinary leakage from the urethra. The additional tension of the wall of the urethral canal around the plug body 102 further holds and secures the plug body 102 in the proper position within the urethra. In embodiments, the diameter D1 is between about 3 mm and about 16 mm, such as about 3 mm, 4 mm, 5 mm, 6 mm, 7 mm, 8 mm, 9 mm, 10 mm, 11 mm, 12 mm, 13 mm, 14 mm, 15, mm and 16 mm.

In embodiments, the plug body includes a tab on the trailing end; the tab positioned to fit within a slot in the urethral plug inserter, see FIG. 9. The tab includes a top surface that is relatively parallel to the long (tip-to-tail) axis of the plug body. The tab tapers upward to the top surface from the connection point of the lanyard.

Returning to FIGS. 1A-1C, the lanyard 130 is a flexible string like material used for removal, a portion of which remains outside of the urethra while the plug is "in situ" in the urethra (see FIG. 7). At the end of the lanyard 130 is a stopper. In embodiments, the lanyard 130 is a solid material and made in a unitary body with the plug body and/or the stopper 140.

With reference to FIGS. 3A-3D, the stopper 140 is a flat modified circular shape having a flattened portion with a face 142. The face 142 faces the plug body. The flattened circular portion includes a front face 144 and a rear face 146 that provide a place for the user to grab when removing the device as well as a place for directions and/or sizing information. The face 142 is used to hold the device in place while assembled on the inserter for insertion. As well, the stopper 140 prevents migration of the plug into the urethra while in situ and facilitates removal.

Figure 4:
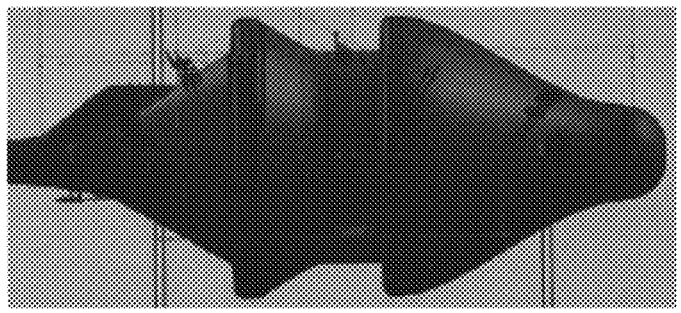
FIG. 4 is a side view of the plug body of a urethral plug having two sealing rings, in accordance with disclosed embodiments.

Referring to FIG. 4, an alternative embodiment is provided showing a side view of plug body that includes two sealing rings. This alternative can be thought of as having two single sealing rings (i.e. a double o-ring) and D1 is the same for the maximum diameter and the trailing o-ring. This iteration of the embodiment was designed to prevent migration in situ. There is a steeper incline at the trailing end of the plug body as the o-ring at the trailing end is the same French size as the maximum diameter. The portion of the plug body immediately before and the sealing ring and after the central extension sized down from the central extension allow a portion of the urethra wall to occupy this depression, which increases the firmness of the seal.

Figure 5:
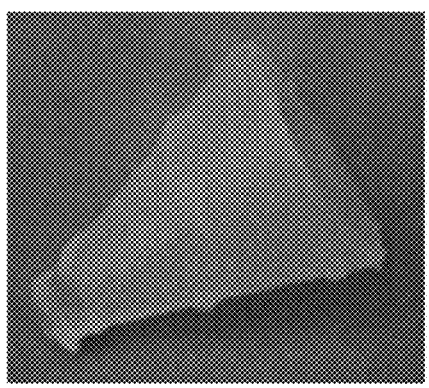
FIG. 5 is a side view of the plug body of a urethral plug having a reversing cone structure, in accordance with disclosed embodiments.

Referring to FIG. 5, an alternative embodiment is provided showing a side view of the plug body of a urethral plug having a reversing cone structure, in accordance with disclosed embodiments. The small end is inserted and as the bulb is pulled back the cone folds over back on itself to create a tight seal. The reversibility of the cone structure ensures that the pointed end of the cone is facing the direction of travel of the device aiding in insertion and removal. The expandable cone also provided maximum expansion in the urethra to help with occlusion.

Figure 6:
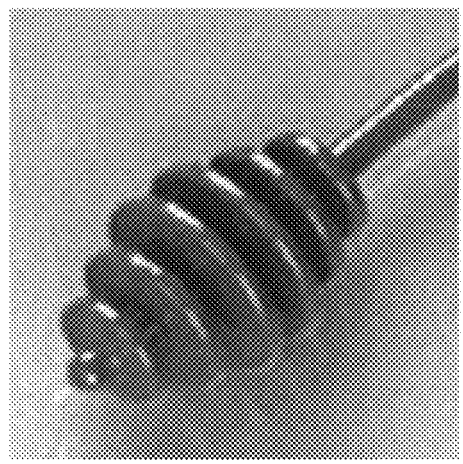
FIG. 6 is a side view of the plug body of a urethral plug having several sealing rings, in accordance with disclosed embodiments.

Referring to FIG. 6, an alternative embodiment is provided showing a side view of the bulb end of a urethral plug having a honey dipper/helix design. This embodiment is meant to fold back on insertion and removal in the director of travel to facilitate easy insertion/removal and to provide and expanded device while in situ to maximize the ability of the plug body to occlude. The rings of the body are flexible enough to collapse during insertion and removal. The lanyard, stopper and other aspects of the base design, sizing convention, surface finish, material, standard length of lanyard, plug body length/diameter varies by size, etc. hold for this alternative embodiment.

Figure 7A:
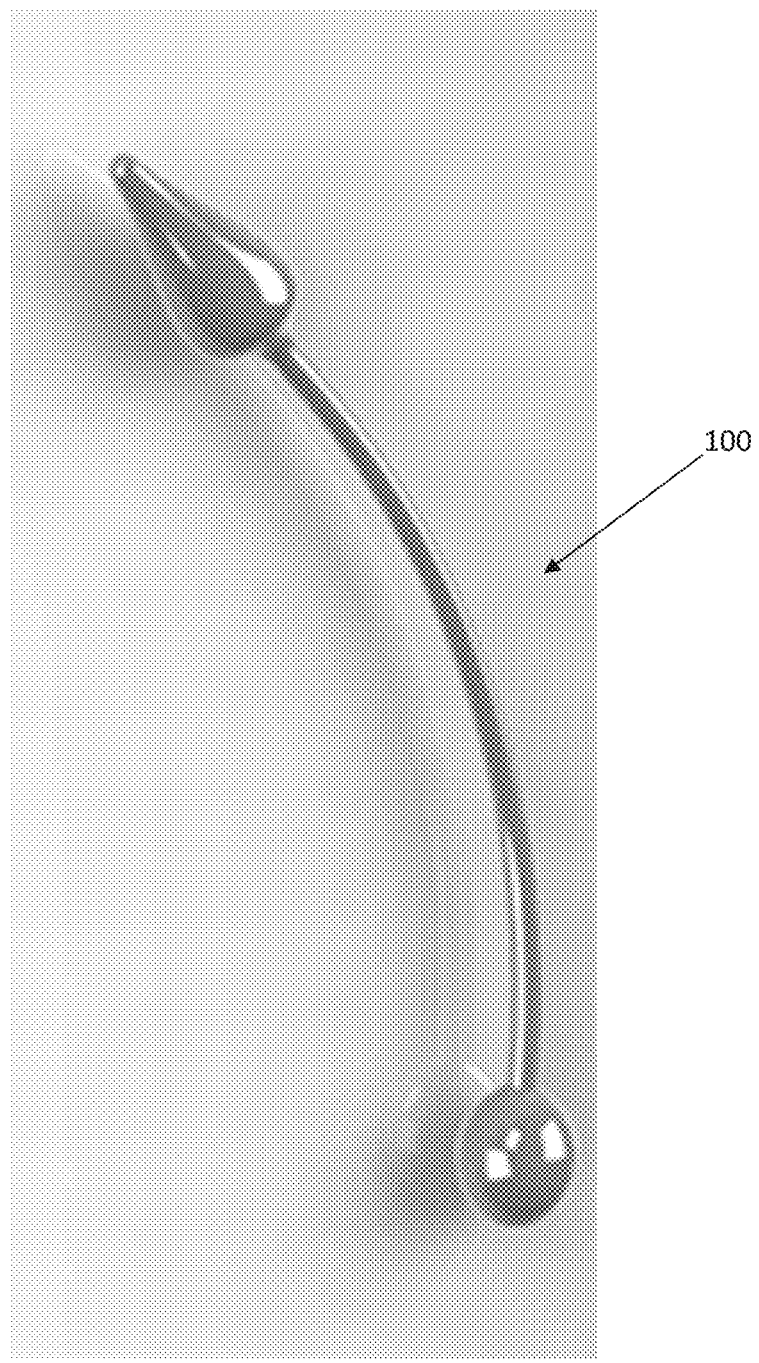
FIG. 7A is a side view of a soft urethral plug, in accordance with disclosed embodiments.
Figure 7B:
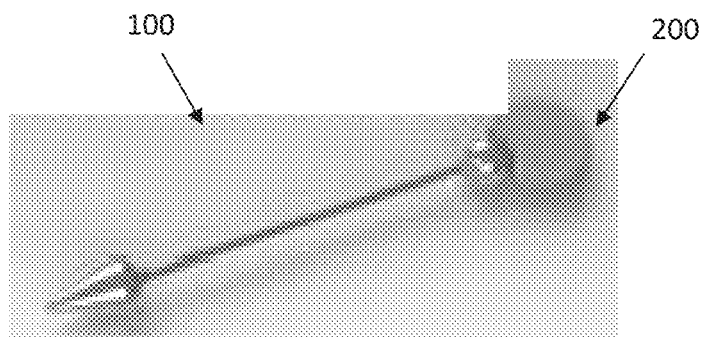
FIG. 7B is a side view of a soft urethral plug with an internal inserter, in accordance with disclosed embodiments.
Figure 7C:
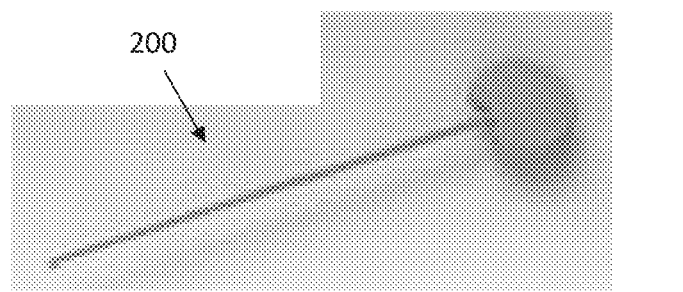
FIG. 7C is a side view of a soft urethral plug internal inserter, in accordance with disclosed embodiments.
Figure 7D:
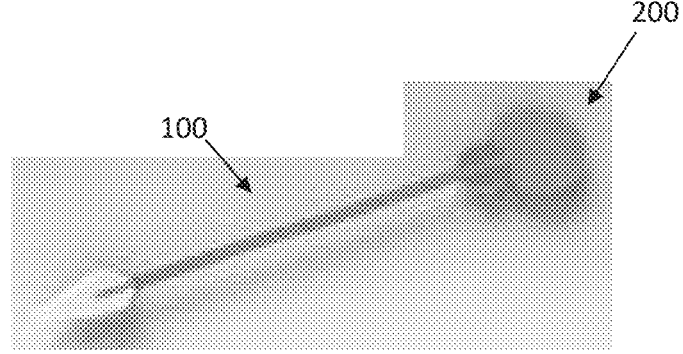
FIG. 7D is a cross sectional view of a soft urethral plug with an internal inserter, in accordance with disclosed embodiments.
Figure 7E:
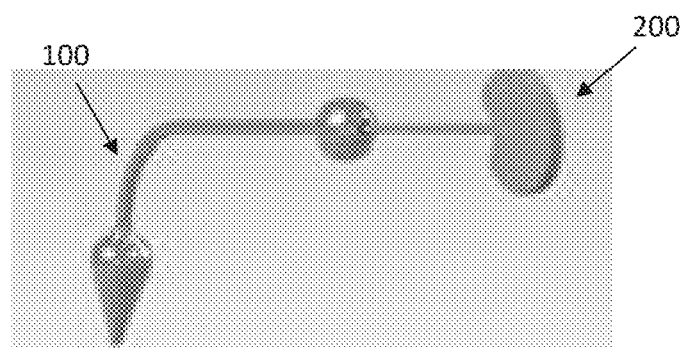
FIG. 7E is a side view of a soft urethral plug with an internal inserter partially inserted into the lanyard of the urethral plug, in accordance with disclosed embodiments.

Referring to FIGS. 7A-7E, an alternative embodiment is provided showing a side view of the inserting tool. This embodiment is meant to have the inserting tool mate with the plug through a hollow tube in the lanyard. FIG. 7A is a side view of a soft urethral plug. FIG. 7B is a side view of a soft urethral plug with an internal inserter. FIG. 7C is a side view of a soft urethral plug internal inserter. FIG. 7D is a cross sectional view of a soft urethral plug with an internal inserter. FIG. 7E is a side view of a soft urethral plug with an internal inserter partially inserted into the lanyard of the urethral plug, in accordance with disclosed embodiments. With reference to FIGS. 7A-7E, the urethral plug 100 is made with a hollow center, into which inserter 200 can be inserted to guide the urethral plug into the urethra of a user. Once properly inserted and placed in the urethra of a user the inserter 200 is removed. In embodiments, the lanyard and plug body have an internal channel configured to hold an internal inserter.

Figure 8:
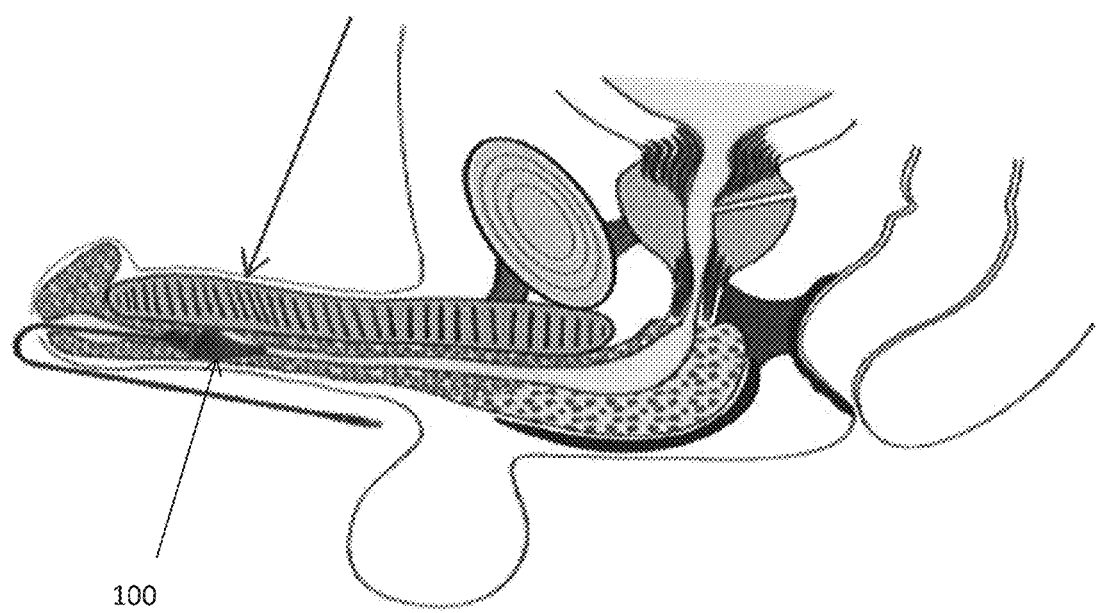
FIG. 8 is a diagrammatic illustration of the urethral plug inserted in the urethra of a male.

With reference to FIG. 8, the urethral plug 100 is shown inserted into and positioned in a male subject's urethra. The urethral plug 100 is assembled with the inserter (not shown) optionally with a lubricant, such as on the outer surface of the leading end. The user can grasp the inserter and insert the leading end into the urethral meatus. The lubricant is preferably a water-based or water-soluble personal lubricant. A person skilled in the art will understand that any type of personal lubricant that provides low surface tension, has good wetting characteristics and dissipates within the urethral canal can be used to lubricate the urethral plug 100 prior to insertion. Insertion of the urethral plug 100 to the proper position is easily accomplished by the user by lightly pushing and rotating the mated inserter and device with the leading end is abutting the urethral meatus. In some examples, the user lubes the meatus and then rotates the device in the meatus to properly lube the plug body so both surfaces are lubricated prior insertion. The proper position for the plug body enables the plug body to reside entirely within the urethra, as shown. When the user is inserting the plug body up the urethral canal, the user hits an area of diminished resistance, at which point, the user stops pushing the inserter, disengages the stopper from the end of the inserter, and withdraws the inserter from the urethral canal. Once the inserter is removed from the urethral canal, the plug body, with a portion of the lanyard, is disposed within the urethra, and the other portion of the lanyard and the stopper are exposed and extend outward from the urethral meatus. At this point, if not previously anchored, the user grasps the lanyard and pulls slightly to move the device within the urethra until an increase in resistance is felt by the user. The slight withdrawal of the device causes the wall of the urethra to gather and fold around the device, which facilitates the anchoring of the device within the urethra. The gathering and folding of the urethral wall around the plug body of the device creates a frictional force between the plug body and the urethral wall.

Similarly, the removal of the device from the urethral canal can be easily done by the user. When the user is ready to remove the device, the user simply pulls upward on the lanyard, for example, on the stopper with the penis extended and also pointing upward. There typically is trapped urine within the urethra that will need to be poured out after the removal and prior to, or during voiding by the user. This action will cause the device to be comfortably and easily withdrawn from the urethra. The user can re-insert the same device using the method set out above. Prior to re-insertion, the device is cleaned with soap and water. Cool tap water is generally sufficient lubrication for re-insertion of device; however, a user may apply lubricant to the meatus and rotate the mated device in the meatus to apply lubricant to the plug body prior to re-insertion.

In the male, as shown in FIG. 8, the device is positioned in the penile urethra, proximate to the membranous urethra, and is well upstream of the urethral meatus and well downstream of the bladder.

Figure 9A:
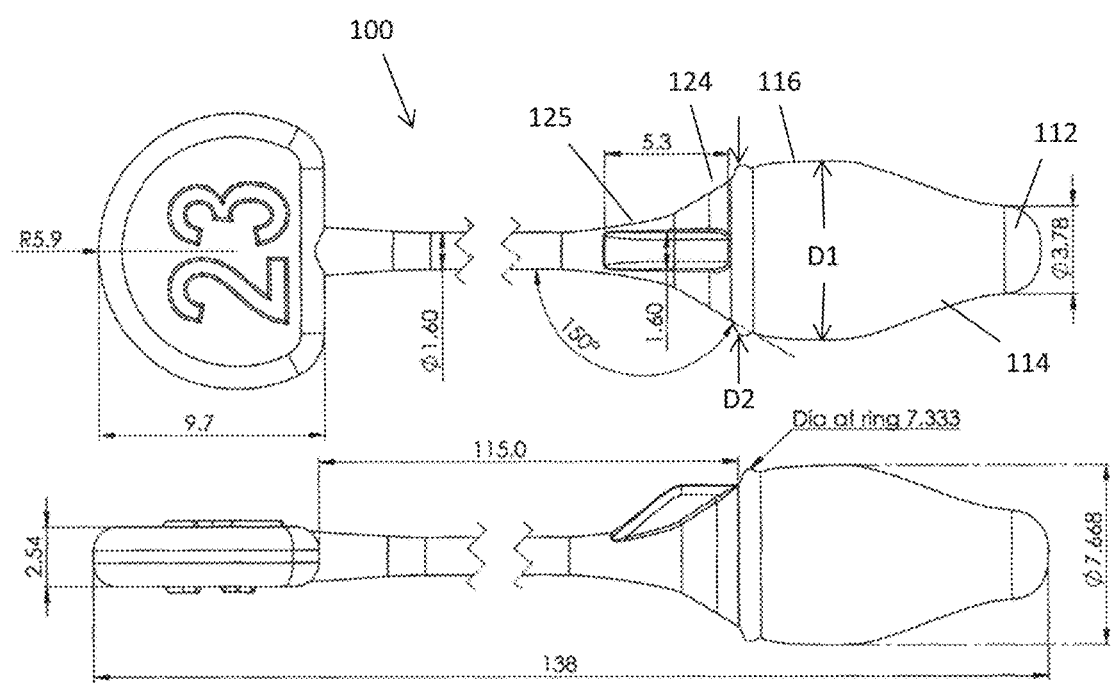
FIGS. 9A and 9B are views showing the relative comparison of the size of small and large urethral plugs, in accordance with disclosed embodiments.
Figure 9B:
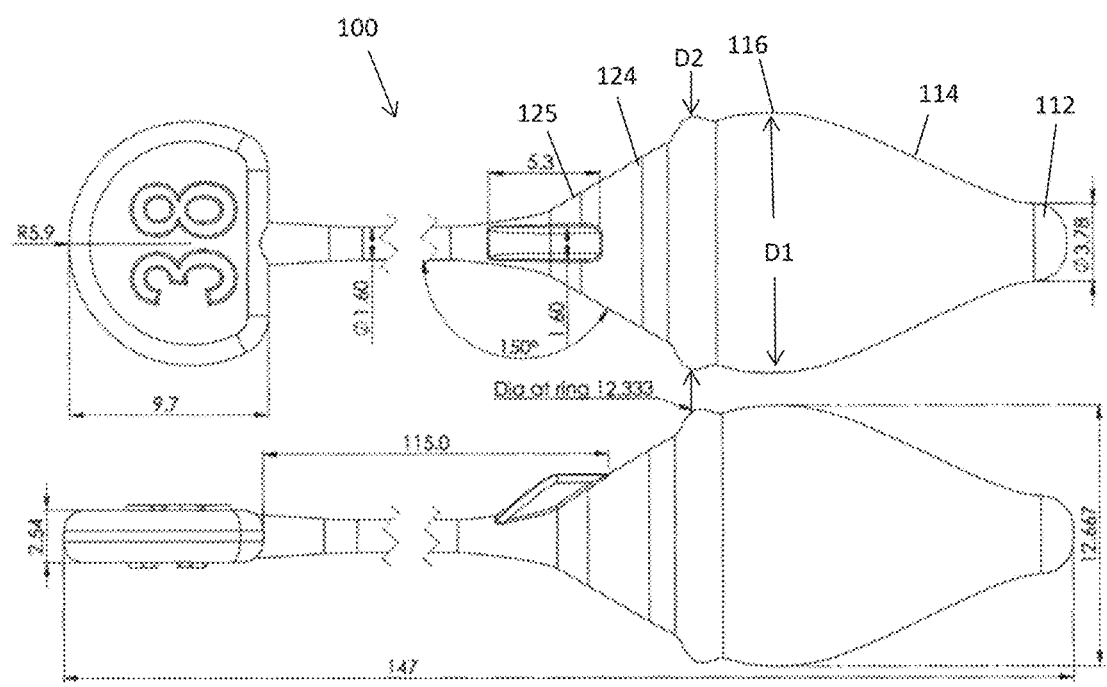

FIGS. 9A and 9B are views showing the relative comparison of the size of small and large urethral plugs, in accordance with disclosed embodiments. Sizing for the user is determined using the sizing tool, which determines the starting French size to begin the trial and error process. As the device is designed to occlude soft tissue that is distensible and not necessary uniformed across all users there is a settling in period for over the course of the first few uses. In terms of the specific sizes 23 F to 38 F devices everything is the same except for the differences with the plug body to be described below and labelling on the stopper, which represents the different sizes. The maximum diameter D1 defines the size of the device (using the French system) and D2 is one French less than D1 for each size. Typically, section 112, 120, 125 and 128 on the plug body are identical for all sizes. The slope and length of 114, 118 and 124 vary according to the size. Starting from the smallest device which is size 23, the angle of the slope and the length of 114 increases as the size increases. The design theme was to make the rise in the slope from 112 to 116 as uniformed, as this is a tissue spreader, across all sizes, so the length was varied to keep the angle of the sloped relatively uniform. From point 116 to 122 that slope decreases (maintaining the same orientation) and the length of section 118 and 124 also increase as the sizes increase. A difference in the overall length of the different sizes relates to changes in length of 114, 118 and 124.

Figure 11:
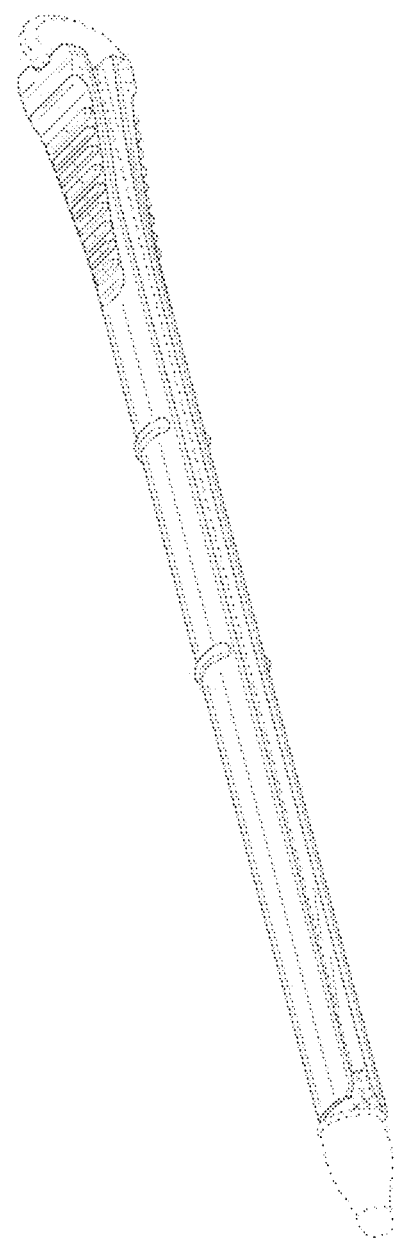
FIG. 11 depicts an inserter for use with the disclosed urethral plug with the urethral plug coupled thereto.

FIGS. 10 and 11 depict an inserter for use with the disclosed urethral plug. As shown, the inserter has a central channel for holding a urethral plug to be inserted into the urethra of a user.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A urethral plug for insertion in a urethra of a male subject, the device comprising:
   a plug body, wherein the plug body comprises:
      a leading end shaped to spread tissue of the urethra upon insertion into the urethra of the male subject;
      a central bulbous portion;
      a trailing end tapering down from the central portion, the central portion disposed between the leading end and the trailing end;
      a sealing ring encircling the central bulbous portion at an intersection location between the trailing end and the central portion;
   a lanyard having a first end and a second end, the first end coupled to the trailing end of the plug body, and wherein the plug body is shaped such that when positioned within the urethra the plug body is retained within the urethra, to restrict urine flow within the urethra past the plug body.

2. The urethral plug of claim 1, further comprising a stopper coupled to the second end of the lanyard wherein, when the device is in situ, a portion of the lanyard and the stopper are located outside a user.

3. The urethral plug of claim 2, wherein the plug body, the lanyard, and the stopper are a unitary body of continuous material.

4. The urethral plug of claim 2, wherein the plug body, the lanyard, and the stopper comprise a thermoplastic polymer.

5. The urethral plug of claim 4, wherein the thermoplastic polymer has durometer hardness of between 50 and 90.

6. The urethral plug of claim 1, wherein the plug body has an outer surface enabling development of friction between the outer surface and a wall of a user's urethra, when the device is in situ, to maintain position of the urethral plug.

7. The urethral plug of claim 1, wherein the plug body comprises a hydrophilic material.

8. The urethral plug of claim 1, wherein the plug body has a surface finish ranging from B-1 to C-3.

9. The urethral plug of claim 1, further comprising a tab extending from the trailing end of the plug body to constrain and align the urethral plug within an associated inserter.

10. The urethral plug of claim 1, wherein the plug body is dimensioned so as to be completely contained within the user's urethra when the device is in situ.

11. The urethral plug of claim 1, wherein the plug body has limited bend or flex.

12. The urethral plug of claim 1, wherein the plug body is non-hollow.

13. The urethral plug of claim 1, wherein the lanyard and plug body have an internal channel configured to hold an internal inserter.

14. The urethral plug of claim 1, wherein the central portion of the plug body is bulbous with a fixed maximum diameter of 3 to 15 mm.

15. The urethral plug of claim 1, wherein a maximum diameter of the trailing end is greater than a maximum diameter of the lanyard.

16. A reusable urethral plug for insertion and removal from a urethra of a male subject, the device comprising:
  a plug body, wherein the plug body comprises:
    a leading end shaped to spread tissue of the urethra upon insertion into the urethra of the male subject;
    a central bulbous portion;
    a trailing end tapering down from the central portion, the central portion disposed between the leading end and the trailing end;
    a sealing ring encircling the central bulbous portion at an intersection location between the trailing end and the central portion;
  a lanyard having a first end and a second end, the first end coupled to the trailing end of the plug body, and
  wherein the plug body is shaped such that when positioned within the urethra the plug body is retained within the urethra, to restrict urine flow within the urethra past the plug body, wherein the urethral plug is configured for repeated insertion and removal from the urethra for reuse.

17. A method of controlling urinary incontinence comprising:
  introducing the urethral plug of claim 1 into a urethra of a male subject; and positioning the urethral plug in the male subject's urethra.

* * * * *